(12) United States Patent  (10) Patent No.: US 9,179,971 B2
Kirschenman  (45) Date of Patent: Nov. 10, 2015

(54) PRINTED ELECTRODE CATHETER

(71) Applicant: St. Jude Medical Atrial Fibrillation Division, Inc., St. Paul, MN (US)

(72) Inventor: Mark Kirschenman, Waverly, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 150 days.

(21) Appl. No.: 13/764,189

(22) Filed: Feb. 11, 2013

(65) Prior Publication Data

US 2014/0228838 A1    Aug. 14, 2014

(51) Int. Cl.
*A61B 5/042*  (2006.01)
*A61B 18/14*  (2006.01)
*A61N 1/05*  (2006.01)

(52) U.S. Cl.
CPC ........... *A61B 18/1492* (2013.01); *A61B 5/0422* (2013.01); *A61N 1/056* (2013.01)

(58) Field of Classification Search
CPC ............................. A61B 5/0422; A61N 1/056
USPC ............................. 600/374; 606/41; 607/122
See application file for complete search history.

(56) References Cited

U.S. PATENT DOCUMENTS

| | | | |
|---|---|---|---|
| 4,476,872 A * | 10/1984 | Perlin | 600/380 |
| 4,762,135 A * | 8/1988 | van der Puije et al. | 607/116 |
| 5,343,860 A * | 9/1994 | Metzger et al. | 600/380 |
| 5,840,031 A | 11/1998 | Crowley | |
| 6,233,476 B1 | 5/2001 | Strommer et al. | |
| 6,357,447 B1 * | 3/2002 | Swanson et al. | 128/898 |
| 6,498,944 B1 | 12/2002 | Ben-Haim et al. | |
| 6,569,162 B2 * | 5/2003 | He | 606/41 |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,229,437 B2 | 6/2007 | Johnson et al. | |
| 7,263,397 B2 | 8/2007 | Hauck et al. | |
| 7,386,339 B2 | 6/2008 | Strommer et al. | |
| 7,536,218 B2 | 5/2009 | Govari et al. | |
| 7,625,617 B1 * | 12/2009 | Anderson et al. | 428/36.9 |
| 7,686,802 B2 * | 3/2010 | Stevens-Wright | 606/41 |
| 8,147,486 B2 | 4/2012 | Honour et al. | |
| 8,221,408 B2 | 7/2012 | Johnson et al. | |

(Continued)

FOREIGN PATENT DOCUMENTS

WO    2007139479    12/2007
WO    2011031201    3/2011

OTHER PUBLICATIONS

"Cathprint Technology brochure", available at http://cathprint.se/uploads/CathPrint%20Brochure%20-%20Our%20technology.pdf (publication date unknown).

(Continued)

*Primary Examiner* — Lee S Cohen
(74) *Attorney, Agent, or Firm* — Dykema Gossett PLLC

(57) ABSTRACT

An elongate medical device may comprise an elongate tubular body, an electrode, and a trace. The elongate tubular body may comprise a distal end portion and a proximal end portion, the body defining a longitudinal axis. The electrode may comprise electrically-conductive ink extending circumferentially about a portion of the distal end portion. The trace may comprise electrically-conductive ink, electrically coupled with the electrode, extending proximally from the electrode.

19 Claims, 12 Drawing Sheets

(56) References Cited

U.S. PATENT DOCUMENTS

| | | |
|---|---|---|
| 8,295,902 B2 * | 10/2012 | Salahieh et al. .............. 600/374 |
| 8,467,844 B2 * | 6/2013 | Rea et al. ...................... 600/380 |
| 2003/0195406 A1 * | 10/2003 | Jenkins et al. ................ 600/374 |
| 2005/0065508 A1 | 3/2005 | Johnson et al. |
| 2007/0060833 A1 | 3/2007 | Hauck |
| 2009/0143651 A1 | 6/2009 | Kallback |
| 2009/0227885 A1 * | 9/2009 | Lowery et al. ................ 600/526 |
| 2009/0247993 A1 | 10/2009 | Kirschenman et al. |
| 2010/0022950 A1 * | 1/2010 | Anderson et al. ........ 604/100.01 |
| 2010/0318019 A1 * | 12/2010 | Nee et al. ........................ 604/21 |
| 2012/0029504 A1 | 2/2012 | Afonso et al. |
| 2012/0143298 A1 | 6/2012 | Just |
| 2012/0172696 A1 | 7/2012 | Kallback |
| 2013/0172715 A1 | 7/2013 | Just |
| 2013/0184549 A1 * | 7/2013 | Avitall et al. ................. 600/373 |
| 2014/0005508 A1 * | 1/2014 | Estes et al. .................... 600/347 |
| 2014/0088591 A1 | 3/2014 | Just |
| 2014/0142409 A1 * | 5/2014 | Garcia et al. .................. 600/383 |

OTHER PUBLICATIONS

International Search Report, PCT/US2015/013308.
Written Opinion of International Search Report, PCT/US2015/013308.

* cited by examiner

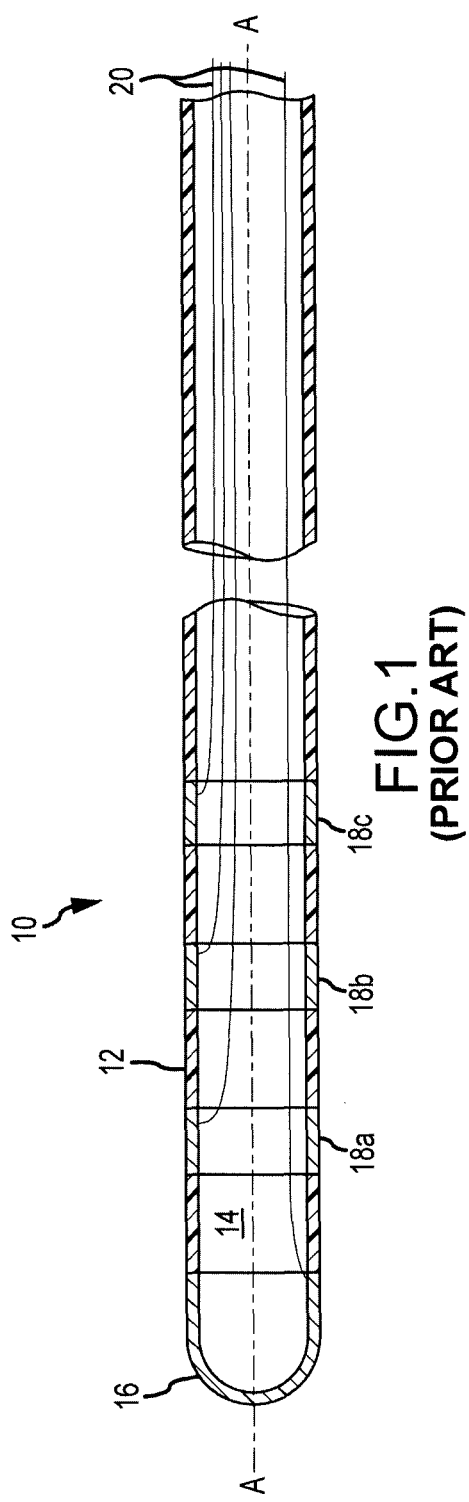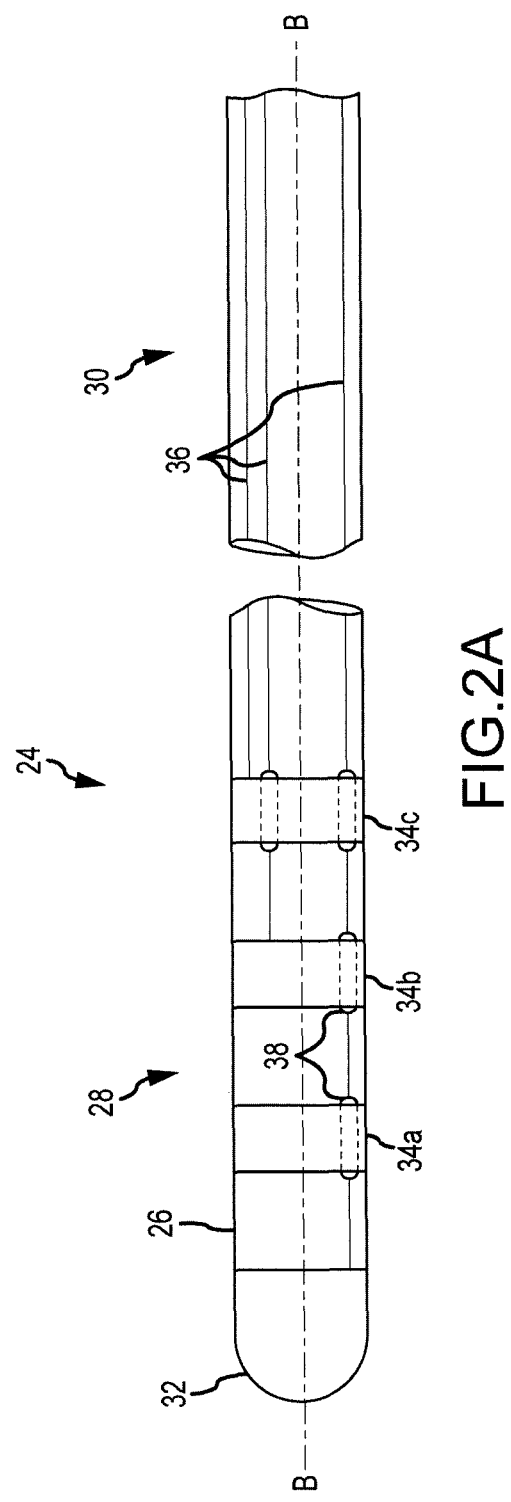

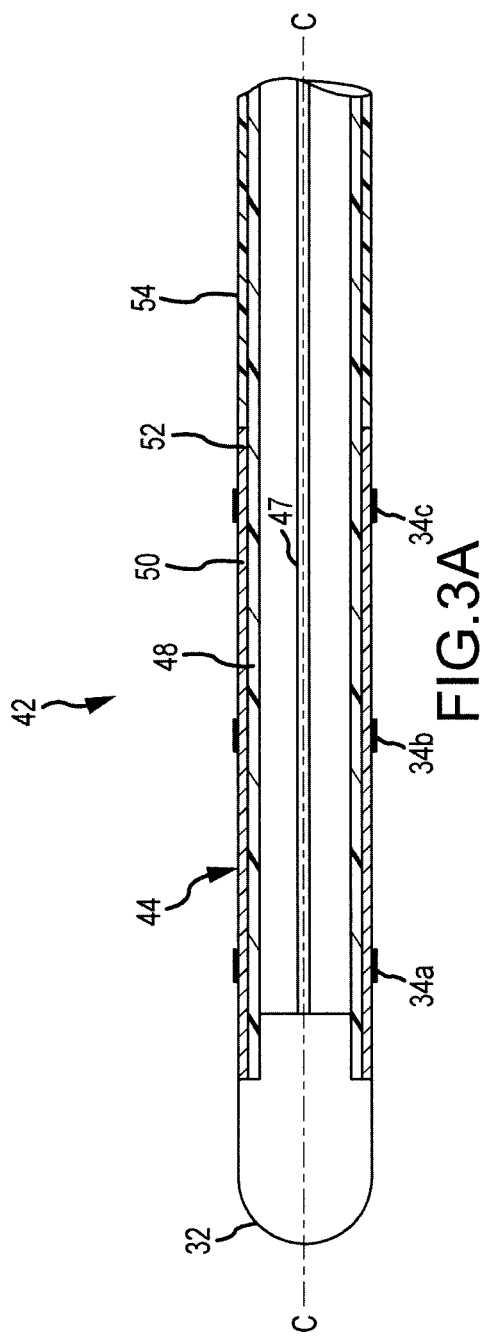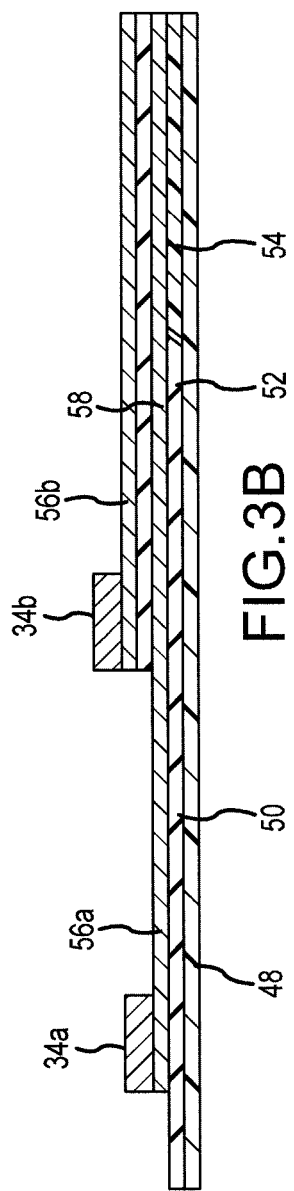

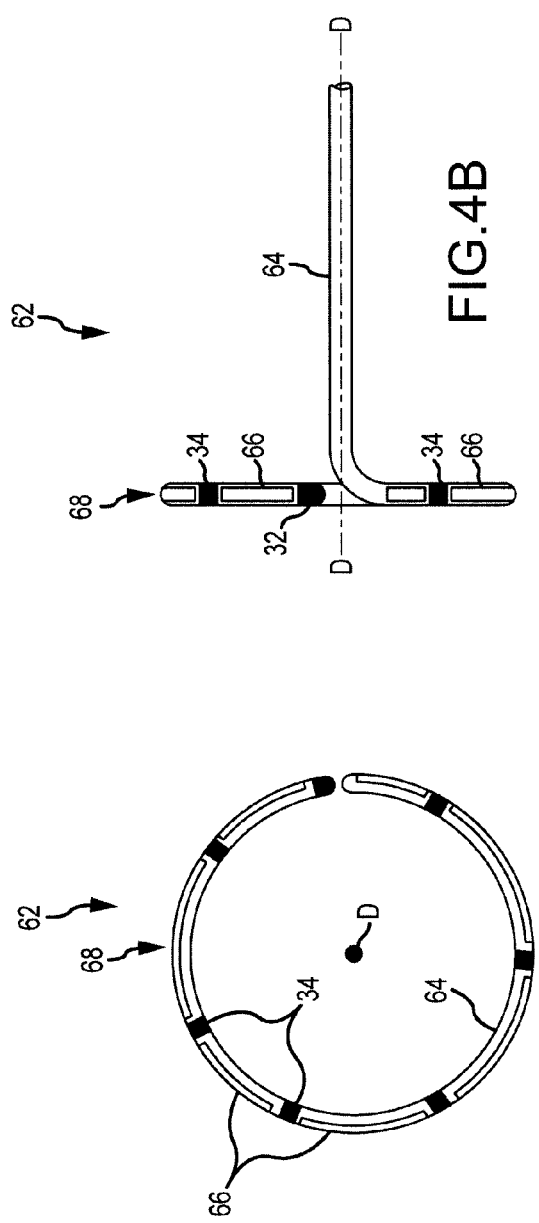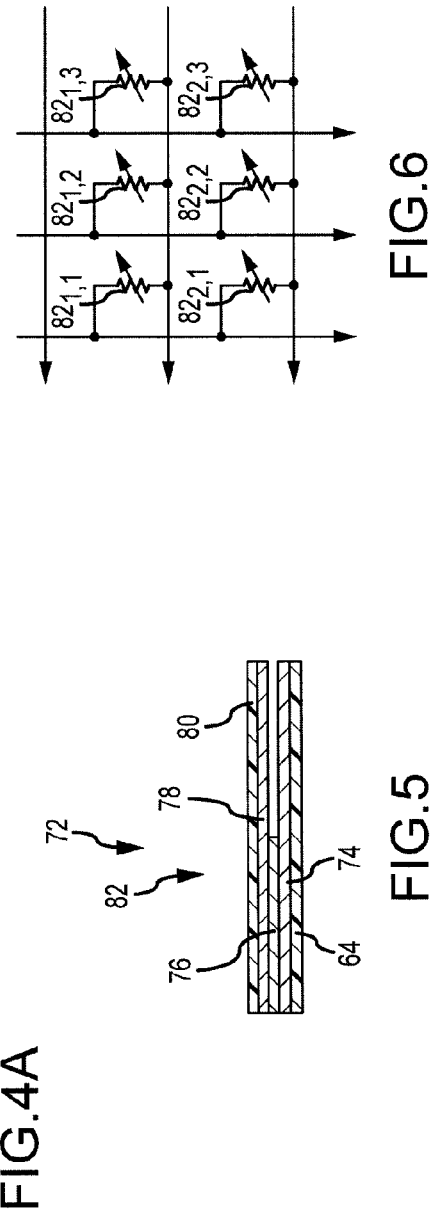

PRINTED ELECTRODE CATHETER

BACKGROUND a. Field of the Disclosure

The instant disclosure relates to elongate medical devices, including the electrical infrastructure for elongate medical devices.

b. Background Art

Electrophysiology catheters are used for an ever-growing number of procedures. For example, electrophysiology catheters are used for diagnostic, therapeutic, and ablative procedures, to name just a few examples. Typically, the catheter is manipulated through the patient's vasculature and to the intended site, for example, a site within the patient's heart. The catheter typically carries one or more sensors, such as electrodes, which may be used for ablation, electrophysiology mapping, and the like.

A portion of an exemplary electrophysiology catheter 10 manufactured according to known methods is shown in cross-section in FIG. 1. The catheter 10 includes an elongate tubular body 12 defining a longitudinal axis A and an interior lumen 14, a tip electrode 16, and a number of ring electrodes 18a, 18b, 18c. The catheter 10 may also include numerous other features (not illustrated), such as one or more pull wires coupled with the body, such as through one or more pull rings, to steer the catheter 10, one or more fluid ports and lumens, and other known features. The body 12 may be made of a thermoplastic elastomer or another suitable material, such as Pebax™, Teflon™, or Kapton™. The ring electrodes 18 may be embedded in the body 12 during melt processing of the body 12 or through other known manufacturing steps or methods. The tip electrode 16 and the ring electrodes 18 may be electrically coupled with leads 20 extending to a proximal end of the catheter (not shown) for coupling with a mapping and navigation system, ablation generator, or other electrical system, for example. The leads 20 may extend longitudinally through the interior lumen 14 of the body, as shown in FIG. 1, or may extend through the wall of the body 12.

The foregoing discussion is intended only to illustrate the present field and should not be taken as a disavowal of claim scope.

BRIEF SUMMARY

An embodiment of an elongate medical device may comprise an elongate tubular body, an electrode, and a trace. The elongate tubular body may comprise a distal end portion and a proximal end portion, the body defining a longitudinal axis. The electrode may comprise electrically-conductive ink extending circumferentially about a portion of the distal end portion. The trace may comprise electrically-conductive ink, electrically coupled with the electrode, extending proximally from the electrode.

Another embodiment of an elongate medical device may comprise an elongate tubular body comprising a distal end portion and a proximal end portion, the body defining a longitudinal axis, a first electrode, and a first trace. The first electrode may comprise electrically-conductive ink extending circumferentially about a first portion of the tubular body. The first trace may comprise electrically-conductive ink, electrically coupled with the first electrode, extending proximally from the first electrode. An electrically insulating layer may be radially inward of the first electrode and the first trace. The elongate medical device may further comprise a second electrode and a second trace. The second electrode may comprise electrically-conductive ink extending circumferentially about a second portion of the tubular body. The second trace may comprise electrically-conductive ink, electrically coupled with the second electrode, extending proximally from the second electrode. At least a portion of the second trace may be disposed radially inward of the electrically insulating layer.

Another embodiment of an elongate medical device may comprise an elongate tubular body comprising a distal end portion and a proximal end portion, the body defining a longitudinal axis, an electrode, a trace, and a force sensor. The electrode may comprise electrically-conductive ink extending circumferentially about a portion of the tubular body. The trace may comprise electrically-conductive ink, electrically coupled with the electrode, extending proximally from the electrode. The force sensor may comprise a semiconducting layer radially between a first electrically-conductive layer and a second electrically-conductive layer.

BRIEF DESCRIPTION OF THE DRAWINGS

FIG. 1 is a cross-sectional view of an embodiment of a portion of a catheter constructed according to known methods.

FIG. 2A is a plan view of an embodiment of a portion of a catheter including electrodes and traces comprising printed ink.

FIG. 3A is a partial cross-sectional view of an embodiment of a portion of a catheter including electrodes and traces comprising printed ink.

FIG. 3B is an enlarged cross-sectional view of an electrical infrastructure portion that may be used to construct the catheter of FIG. 3A.

FIGS. 4A and 4B are orthogonal plan views of an embodiment of a portion of a catheter including electrodes, traces, and contact sensors comprising printed ink.

FIG. 5 is an enlarged cross-sectional view of a contact sensor comprising printed ink that may be included in the catheter of FIGS. 4A and 4B.

FIG. 6 is a schematic view of an exemplary contact sensing circuit.

DETAILED DESCRIPTION

Figure 2B:
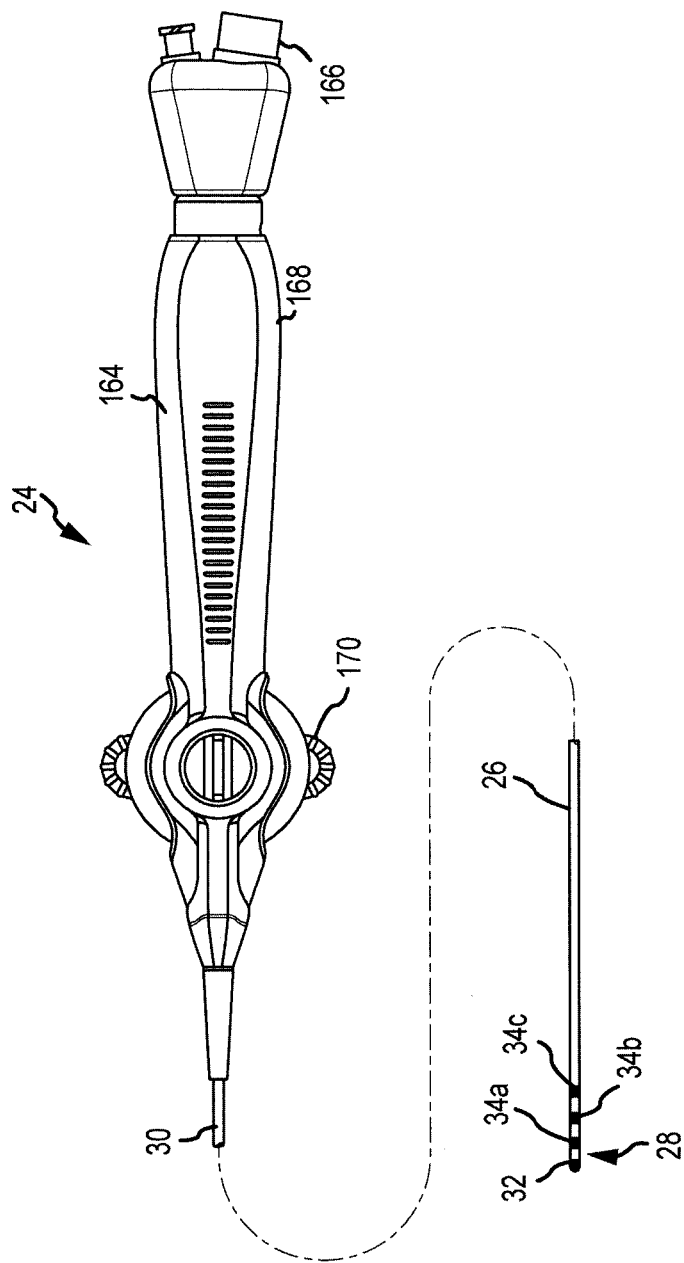
FIG. 2B is a plan view of the catheter of FIG. 2A.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

The manufacture of electrophysiology catheters according to known methods, such as the catheter 10 shown in FIG. 1, presents certain difficulties. For example, the large number of wires (e.g., pull wires and electrical leads for numerous electrodes) and potential for breakage of any of those wires may result in difficulty routing the wires through the numerous internal features of the catheter and handling of those wires during manufacturing. Therefore, according to at least one embodiment, a method for simplifying the construction and manufacturing of the catheter includes replacing known electrodes and leads with electrodes and leads comprising conductive ink printed directly on one or more layers of the catheter body.

Referring again to the Figures, in which like reference numerals refer to the same or similar features in the various views, FIG. 2A is a plan view of an embodiment of a portion of an elongate medical device 24. The medical device 24, like all ell elongate medical devices shown and described herein, may be a catheter, introducer, or other elongate medical device type. The elongate medical device 24, like all elongate medical devices shown and described herein, will be referred to as a catheter for ease of description (i.e., catheter 24). It should be understood, though, that the elongate medical device 24, like all elongate medical devices described herein, is not limited to a catheter.

The catheter 24 may include an elongate tubular body 26 defining an axis B and having a distal end portion 28 and a proximal end portion 30, a tip electrode 32, a number of ring electrodes 34a, 34b, 34c, a number of electrically-conductive traces 36, and a number of masks 38. The traces 36 may each be electrically coupled to a respective one of the tip electrode 32 and the ring electrodes 34 for electrically connecting the respective electrode 32, 34 to, for example, a mapping and navigation system, an ablation generator, and/or another known electrical system. Though not shown, the traces 36 may be radially covered by an outer layer of the body, in an embodiment.

Each of the ring electrodes 34 may extend about the entire circumference of the body 26, in an embodiment. In other embodiments, one or more of the ring electrodes 34 may extend about only a portion of the circumference of the body 26. Each of the traces 36 may extend proximally from a respective one of the electrodes 32, 34 over the longitudinal length of the body 26. At the proximal tip of the body (not shown), each of the traces 36 may be electrically coupled with a lead extending through a handle that is coupled with the body 26.

The tip electrode 32 may comprise a unitary metal element coupled with the body, in an embodiment. In other embodiments, the tip electrode 32 may comprise printed ink, like the ring electrodes 34, as described below.

The ring electrodes 34 and traces 36 may comprise electrically-conductive printed ink, in an embodiment. Like all printed ink elements shown and/or described herein, the ring electrodes 34 and traces 36 may be deposited or printed directly on the body 26, in an embodiment, according to an ink printing or deposition process, such as aerosol jet deposition, for example. The ring electrodes 34 and traces 36 may comprise the same materials (i.e., the same types of ink), in an embodiment. In other embodiments, the ring electrodes 34 and traces 36 may comprise different materials (i.e., different types of ink). Different inks may be used because different properties may be desirable and/or permissible for the ring electrodes 34 and the traces 36. For example, it may be desirable for the traces 36 to be more flexible to bend as the body 26 bends, while relatively stiffer ring electrodes 34 may be acceptable. In addition, it may be desirable for the ring electrodes 34 to have low impedance for more accurate electrical measurements, while relatively higher impedance traces 36 may be acceptable. Accordingly, a relatively rigid, low impedance metallic ink may be used for the ring electrodes 34 and a more flexible ink such as one comprising nanotubes or graphene, for example, may be used for the traces 36.

The masks 38 may be provided for extending the traces 36 past ring electrodes 34 without electrically coupling a ring electrode 34 with a trace 36 that is coupled with a more distal electrode. For example, three separate masks 38 may prevent the trace 36 that is electrically coupled with the tip electrode 32 from being electrically coupled with the first, second, and third ring electrodes 34a, 34b, 34c, respectively.

FIG. 2B is a plan view of catheter 24. In addition to the elements described in conjunction with FIG. 2A, the catheter 24 may include a handle assembly or handle 164 coupled with the catheter body 26 and one or more electromechanical connectors 166 configured to allow the catheter 24, and the electrodes 32, 34 thereof, in particular, to be coupled with components or subsystems of, for example, an electrophysiology (EP) laboratory system. Such components or subsystems may comprise, for example and without limitation, a visualization, navigation, and/or mapping system, an EP monitoring and recording system (e.g., for monitoring and/or recording electrocardiograms (EGM), cardiac signals, etc.), a tissue contact sensing system, an ablation system, a cardiac stimulation system (i.e., EP stimulator), and the like. An exemplary system is shown in U.S. patent application publication no. 2012/0029504, which is hereby incorporated by reference in its entirety as though fully set forth herein.

The handle 164 may be disposed at the proximal end portion 30 of the shaft body portion 26. The handle 164 may provide a location for the clinician to hold the catheter 24 and may further provide means for steering or guiding the shaft body 26 within the body of a patient.

The handle 164 may comprise a housing 168. The housing 168 may be of a unitary construction or may be constructed of a plurality of pieces that are configured to be assembled together. In a multi-piece embodiment, the housing 168 may be coupled together in any number of ways known in the art, such as, for example, by press fit or interference coupling techniques, by complementary interlocking members, by conventional fasteners or adhesives, or any other techniques known in the art.

In addition to the components described above, in an exemplary embodiment, the catheter 24 may further comprise a deflection mechanism 170 associated with the handle 164 of the catheter 24. The deflection mechanism 170 may be coupled with a pull assembly (not shown) disposed at or in the distal end portion 28 of the shaft body 26. The combination of the deflection mechanism 170 and the pull assembly provides a means by which a user or physician can effect movement (e.g., deflection) of the distal end portion 28 in one or more directions, and therefore, allows the physician to steer the catheter 24.

FIG. 3A is a partial cross-sectional view of another embodiment of a portion of a catheter 42. The catheter 42 may comprise an elongate tubular body 44 defining an axis C and an interior lumen 46, a tip electrode 32, a number of ring electrodes 34a, 34b, 34c, and an electrical connection 47 extending through the lumen 46. The ring electrodes 34 may each be coupled with a respective electrically-conductive trace, as will be described in conjunction with FIG. 3B. The body 44 may comprise an inner braid layer 48 and an outer polymer layer 50. The outer polymer layer may comprise a distal segment 52 and proximal segment 54. The inner braid layer 48, outer polymer layer 50, and ring electrodes 34 are shown in cross-section.

The distal segment 52 and the proximal segment 54 of the outer polymer layer 50 of the body 44 may comprise different materials, in an embodiment. The distal segment 52 may comprise Teflon™, for example, and the proximal segment may comprise Pebax™, for example. Different materials may be provided, in an embodiment, because deposition or printing of the ring electrodes 34 and/or traces may require curing of the printed ink at a temperature that is higher than the melting point of certain melt-processing polymers. For example, traces coupled with the ring electrodes 34 may comprise carbon nanotube (CNT) printed ink with a cure temperature of about 150° Celcius (C). A polymer comprising the proximal segment 54, such as Pebax™, may have melting a temperature, such as about 130-174° C., that is lower than the temperature required for curing the printed ink. Accordingly, the distal segment 52 may comprise Teflon™, for example, which has a melting temperature of about 320° C., or another suitable material which an acceptably high melting point. In addition, the portions of the traces over the proximal segment 54 may be laser sintered, rather than cured, in an embodiment, to avoid melting the proximal segment 54. The distal segment 52 may be about six centimeters (6 cm) in length, in an embodiment. The length of the distal segment 52 may be selected according to the desired length of the portion of the catheter 42 on which ring electrodes 34 are to be disposed.

FIG. 3B is cross-sectional view of an exemplary electrode and trace infrastructure which may be used, for example, to print the ring electrodes 34 and traces of the catheter 42. The illustrated infrastructure comprises the first ring electrode 34a, the second ring electrode 34b, and first and second traces 56a, 56b electrically coupled with the first and second ring electrodes 34a, 34b, respectively.

The infrastructure may include, in an embodiment, a radial layer for each ring electrode and trace, each separated by an electrically-insulating layer 58. Thus, in an embodiment, the electrically-insulating layer 58 may be radially-inward of the second electrode 34b and the second trace 56b, and a portion of the first trace 56a may be radially-inward of the electrically-insulating layer 58. The ring electrodes 34 and traces 56 may comprise electrically-conductive printed inks substantially as described above. The electrically-insulating layer 58 may comprise acrylic cured with ultraviolet (UV) light (i.e., UV acrylic), in an embodiment, and/or another suitable electrical insulator.

Referring to FIGS. 3A and 3B, in build-up, the electrodes 34, traces 56, and one or more electrically-insulating layers 58 may be deposited or printed in an alternating sequence. For example, a first trace 56a may be deposited in a line along the length of the distal segment 52 of the outer polymer layer 50 of the catheter body 44. The first electrode 34a may then be deposited about the circumference of the body 44, including over a portion of the first trace 56a, such that the first trace 56a and the first electrode 34a are electrically coupled. Next, a first electrically-insulating layer 58 may be deposited over at least a portion of the first trace 56a (i.e., the portion of the first trace 56a not covered by the first electrode 34a) along the length of the catheter body 44 and, in an embodiment, about the circumference of the catheter body 44. A second trace may 56b then be deposited along the length of the first electrically-insulating layer 58, then a second electrode 34b about the circumference of the body 44, and so on for as many ring electrodes 34 are desired. As a result, each of the ring electrodes 34 may each extend about the entire circumference of the body, if desired, and each ring electrode may be electrically coupled to an independent electrical trace 56.

FIGS. 4A and 4B are plan views of an embodiment of a catheter 62. The catheter 62 may comprise an elongate tubular body 64 defining a longitudinal axis D, a tip electrode 32, a number of ring electrodes 34, and a number of resistive or capacitive force sensors 66. For clarity of illustration, not all electrodes 34 or force sensors 66 are designated. A distal end portion 68 of the body 64 (i.e., a portion including the electrodes 32, 34 and force sensors 66) may be configured to curl about the axis D to substantially form a circle about the axis D (FIG. 4A shows the distal end portion 68 only, for clarity of illustration). Such a circular configuration may be desired and used for particular mapping and ablation procedures, among other things. The ring electrodes 34 may comprise printed ink, printed and/or deposited according to one or more methods and/or configurations described herein.

One or more of the force sensors 66 may also comprise printed ink, in an embodiment. A force sensor 66 may comprise, in an embodiment, a semiconductive grid layered between separate conductive layers. FIG. 5 is a cross-sectional view of a portion 72 of a force sensor 66, taken transverse to the length of the force sensor portion. The force sensor portion 72 may include the catheter body 64, a first electrically-conductive printed ink layer 74, a semiconductor printed ink layer 76, a second electrically-conductive printed ink layer 78, and an external electrically-insulating printed ink layer 80.

The grid of the semiconductive layer 76 of the force sensor 66 may include grid lines, with each line having a corresponding conductive grid line on one or both of the conductive layers 74, 78. Each junction point where a grid line from the first conductive layer 74 crosses a grid line from the second conductive layer 78 with a semiconductive grid line in between forms a piezoresistive force sensor. FIG. 5 illustrates one such junction 82. Application of external force to the junction 82 changes the conductance of the junction 82. Each force sensor 66 shown in FIG. 4A may comprise a plurality of sensing junctions 82. In an embodiment, the plurality of sensing junctions 82 may be arranged in a grid, as noted above.

A plurality of force sensor junctions 82 may effectively form an electrical circuit similar to that shown in FIG. 6. The force sensor junctions 82 may be arranged in a plurality of rows (two are shown in FIG. 6) and columns (three are shown in FIG. 6). The rows and/or columns of force sensor junctions 82 may be interrogated (i.e., have their respective resistances/conductances checked), or the sensor junctions may be interrogated individually by, for example, driving a test voltage through a single row and/or a single column at a time while grounding other rows and/or columns. Accordingly, by cycling through the rows and columns in a sequence, each force sensor junction 82 may be interrogated individually (either directly, or indirectly by mathematical combination of row and column measurements) to assess the force at that junction 82. Detected forces may be displayed by a connected mapping and navigation system, for example, to inform a physician of what portions of the catheter 62 are contacting the patient's body.

Force sensors 66 such as those illustrated in FIGS. 4A-6 may be used in a number of applications. For example, a plurality of force sensors 66 may be disposed about the circular portion of a circular mapping catheter, as shown in FIG. 4A. In another application, a plurality of force sensors 66 may be disposed along the length of a sheath or introducer to assess the position of the sheath or introducer relative to a transseptal puncture. Of course, other applications are possible, as well. Accordingly, the features illustrated in FIGS. 4A-6 are not limited to use in the embodiment illustrated in FIGS. 4A-4B.

Figure 7B:
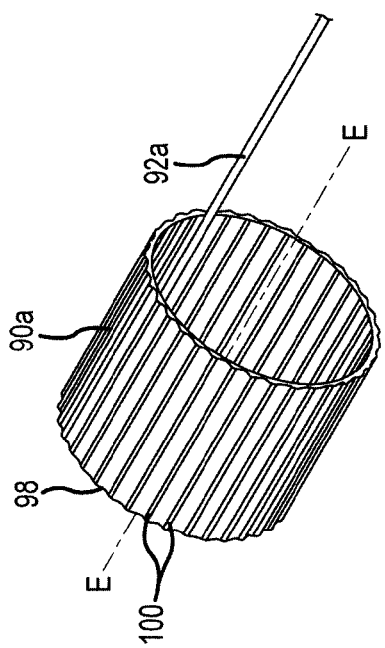
FIG. 7B is an isometric view of an electrode and a portion of a trace of the catheter portion of FIG. 7A.
Figure 7C:
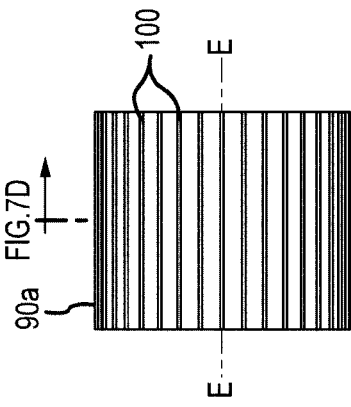
FIG. 7C is a side view of the electrode of FIG. 7B.
Figure 7A:
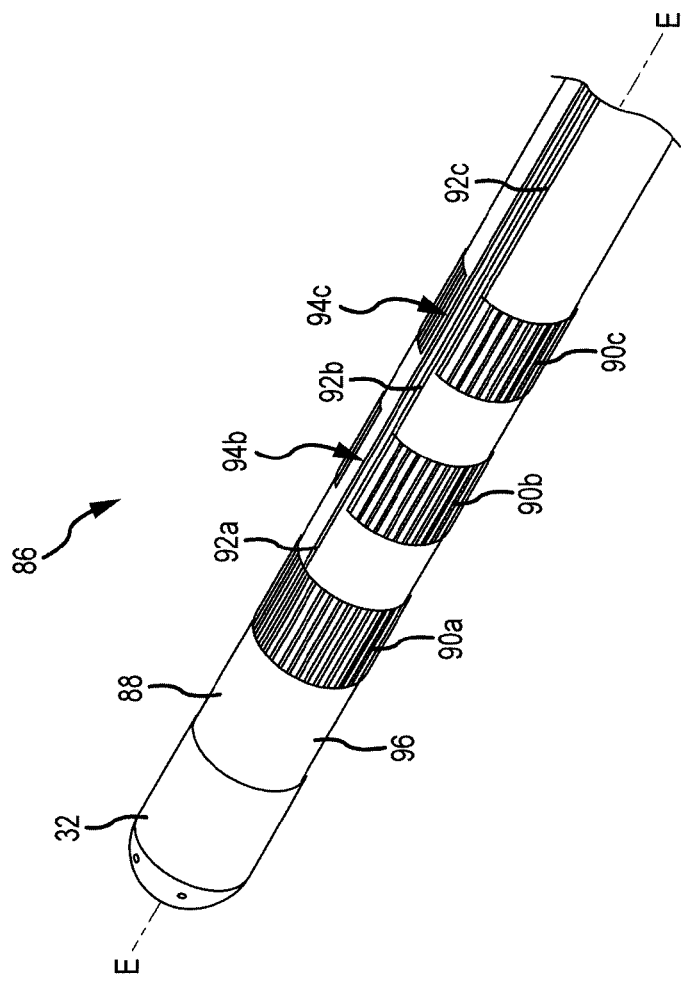
FIG. 7A is an isometric view of an embodiment of a portion of a catheter including electrodes and traces comprising printed ink in a first stage of construction.

FIG. 7A is an isometric view of an embodiment of a catheter 86 in a first stage of construction. The catheter 86 may include an elongate tubular body 88 defining an axis E, a tip electrode 32, a number of ring electrodes 90a, 90b, 90c, and a number of electrically-conductive traces 92a, 92b, 92c. The second and third ring electrodes 90b, 90c do not extend around the entire circumference of the body 88, but instead include respective circumferential gaps 94b, 94c through which traces 92 coupled with more distal electrodes 32, 90 extend.

FIG. 7A illustrates the catheter 86 after the tip electrode 32 has been coupled with the catheter body 88 and the ring electrodes 90 and traces 92 have been printed on a first layer 96 of the catheter body 88. The body first layer 96 may include one or more melt processing polymers and/or another appropriate material, such as Pebax™, Teflon™, or Kapton™. The body first layer 96 may be constructed, in an embodiment, similarly to the catheter body in FIG. 3A (i.e., with a distal segment of a first material and a proximal segment of a second material). The body 88 may also be constructed according to other methods known in the art, in embodiments. The ring electrodes 90 and traces 92 may comprise electrically-conductive printed ink.

FIG. 7B is an isometric view of a first ring electrode 90a and a portion of its trace 92a. FIGS. 7C and 7D are plan views of the first ring electrode 92a. FIG. 7E is an enlarged plan view of a portion of the first ring electrode 92a. Referring to FIGS. 7B-7E, the first ring electrode 92a, like each ring electrode 92, may include a body portion 98 and a plurality of longitudinally-extending ribs 100. In an embodiment, ribs 100 may additionally or alternatively extend circumferentially and/or in another direction or pattern. Furthermore, in addition to or instead of ribs 100, different protrusions or structures may be provided.

The ribs 100 (or other protrusions or patterns) may be provided to increase the surface area of the electrode 92. When measuring the impedance between the electrode 92 and a given point in an electrolyte (i.e., a patient's blood pool), the total impedance can be reduced by increasing the surface area of the electrode 92. Lower impedance, in turn, may allow for more accurate measurements. Accordingly, by providing ribs 100 on the electrode 92a, impedance may be reduced, and measurement accuracy may be improved.

The ribs 100 may be printed, in an embodiment, using a relatively high viscosity ink or multiple layers of ink. The ribs 100 may comprise the same material (i.e., the same ink) as the electrode body portion 98, in an embodiment. The ribs 100 may comprise a different material (i.e., a different ink) than the electrode body portion 98, in other embodiments. The ribs 100 may have a transverse (i.e., transverse to the axis E) height of about 1 thousandth of an inch (0.001 in) or less, in an embodiment, so as not to damage a patients' vasculature.

Figure 7F:
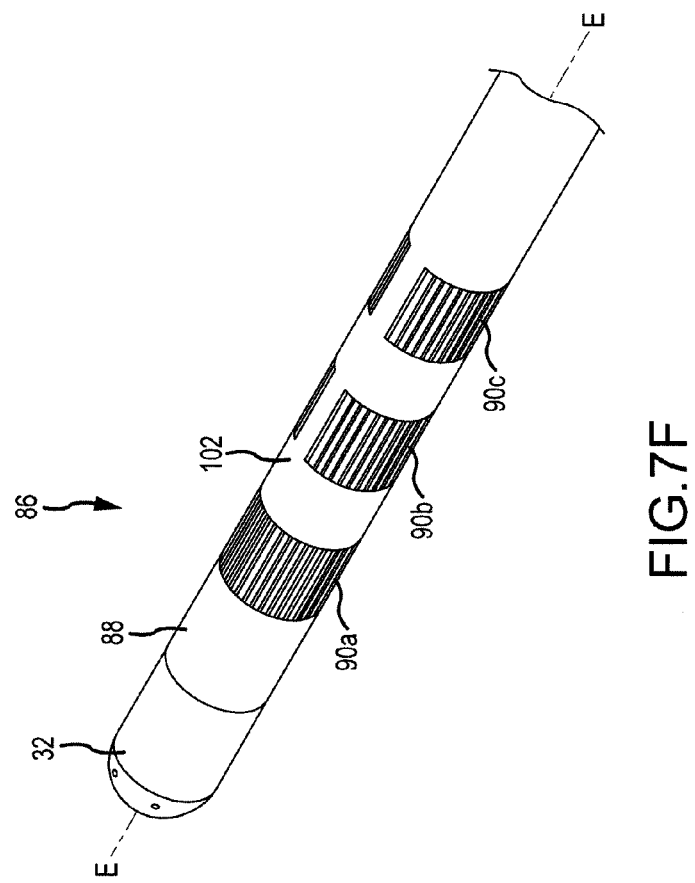
FIG. 7F is an isometric view of the catheter portion of FIG. 7A in a second stage of construction.
Figure 7D:
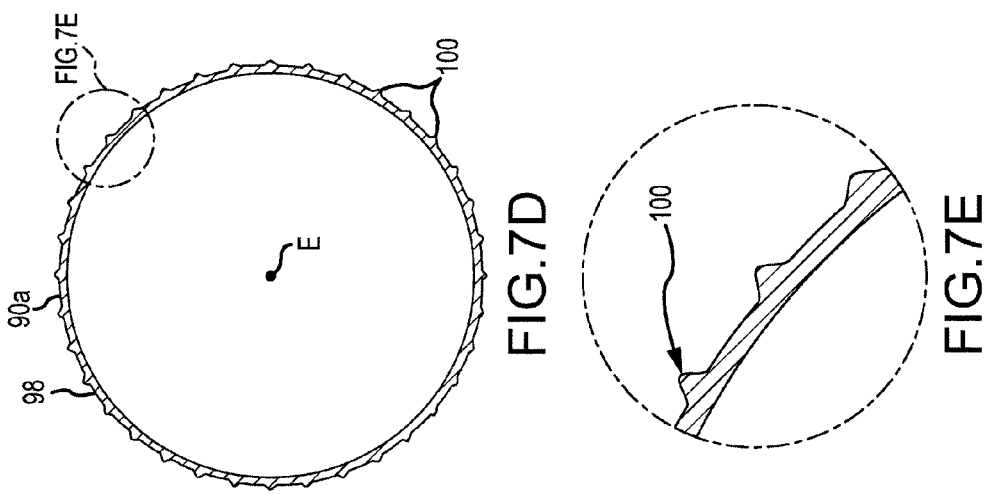
FIG. 7D is a cross-sectional view of the electrode of FIG. 7B.
Figure 7E:
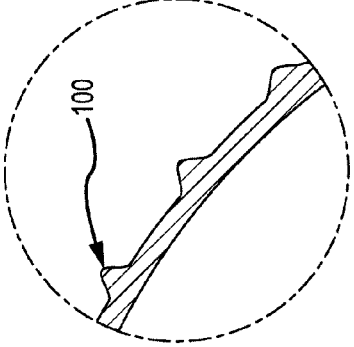
FIG. 7E is an enlarged cross-sectional view of a portion of the electrode of FIGS. 7B-7D.

FIG. 7F is an isometric view of the catheter 86 in a second stage of construction. Referring to FIGS. 7A and 7F, after the ring electrodes 90 and traces 92 have been printed, a second layer 102 of the body 88 may be printed. The second body layer 102 may cover (i.e., be radially-outward of) the traces 92. The second body layer 102 may also cover portions of the first body layer 96 not covered by the ring electrodes 92. In an embodiment, the second body layer 102 may comprise a dielectric ink.

Figure 8A:
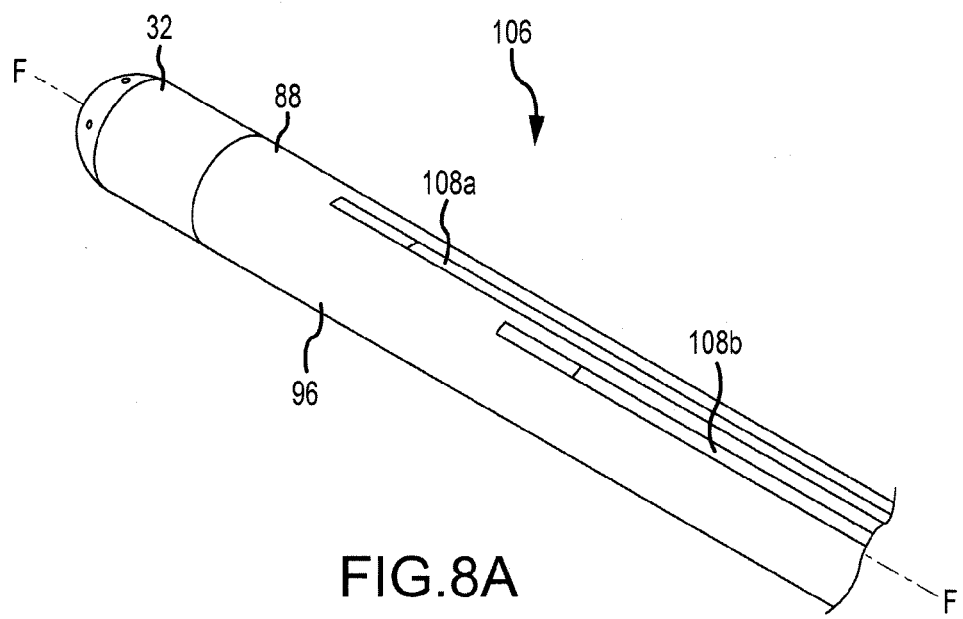
FIGS. 8A-8D are isometric views of an embodiment of a portion of a catheter including electrodes and traces comprising printed ink in various stages of construction.

FIGS. 8A-8D are isometric views of an embodiment of a catheter 106 in various stages of construction. In a first stage, the result of which is shown in FIG. 8A, a first layer 96 of an elongate tubular body 88 defining an axis F may be provided, a tip electrode 32 may be coupled to a distal end of the first layer 96, and electrical traces 108a, 108b may be printed on the first layer 96. The body first layer 96 may comprise Pebax™ or another melt-processing polymer or appropriate material as described herein. The traces 108 may comprise electrically-conductive printed ink, in an embodiment.

Figure 8B:
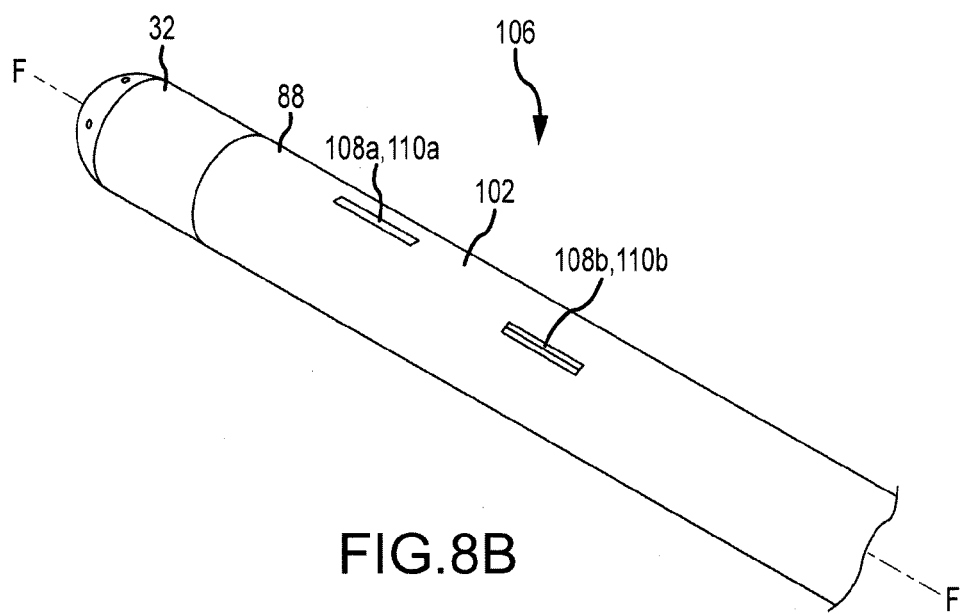

In a second stage of construction, the result of which is shown in FIG. 8B, a second body layer 102 may be printed over most of the traces 108, but for pass-through points 110a, 110b where electrodes will contact the traces 108a, 108b. In an embodiment, the second body layer 102 may be a dielectric printed ink.

Figure 8C:
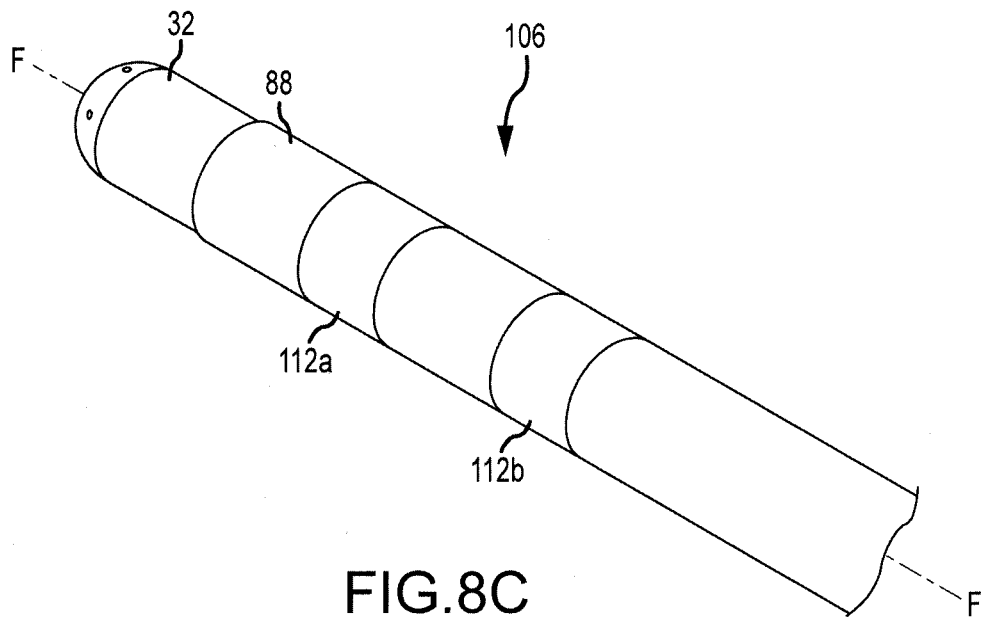

In a third stage of construction, the result of which is shown in FIG. 8C, electrodes 112a, 112b may be printed. The electrodes 112 may comprise electrically-conductive printed ink. Each electrode 112a, 112b may be printed so as to be electrically coupled with a respective one of the traces 108a, 108b. In an embodiment, each electrode 112a, 112b may be printed to cover (i.e., be radially-outward of) a respective trace pass-through 110a, 110b. The electrodes 112 may comprise the same materials (i.e., the same electrically-conductive printed ink or inks) as the traces 108, in an embodiment.

Figure 8D:
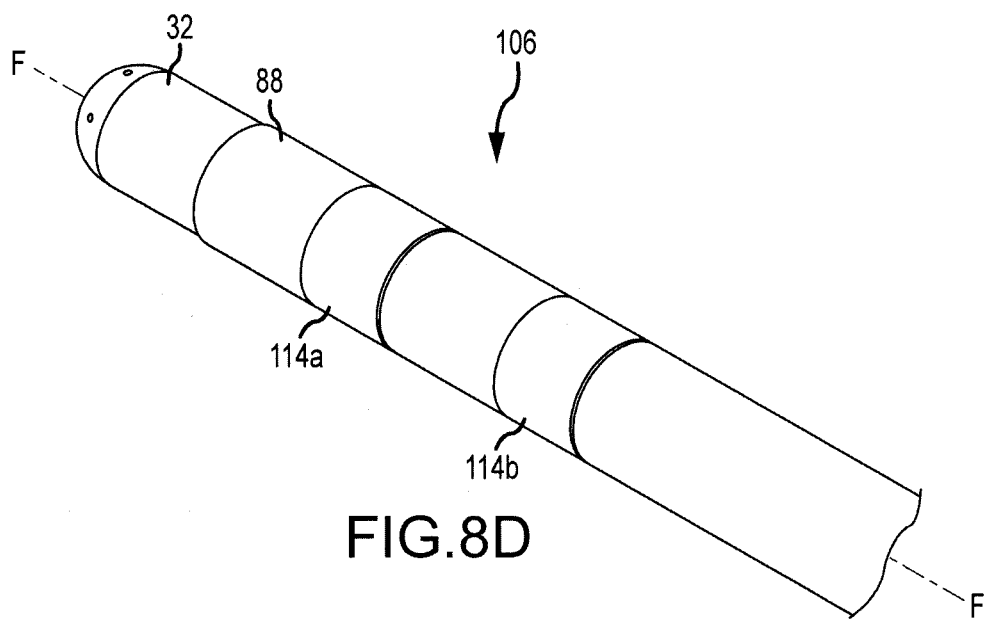

In a fourth stage of construction, the result of which is shown in FIG. 8D, the electrodes 112 may be electroplated with platinum, gold, or another biologically-inert metal to create a metal outer electrode layer 114a, 114b. The printed-ink layer 112 of the electrodes may be used to apply a negative charge to draw in the plating ions during electroplating.

The embodiment of FIGS. 8A-8D may be preferred because it may allow the same materials (i.e., the same printed ink) to be used for the traces 108 and for the electrodes 112, simplifying manufacturing. Because the electroplated metal layer 114 may provide the low-impedance interface desirable for accurate measurements, the electrically-conductive ink used to print the electrodes 112 may be a more flexible, higher-impedance ink that may also be used to print the traces 108.

Figure 9A:
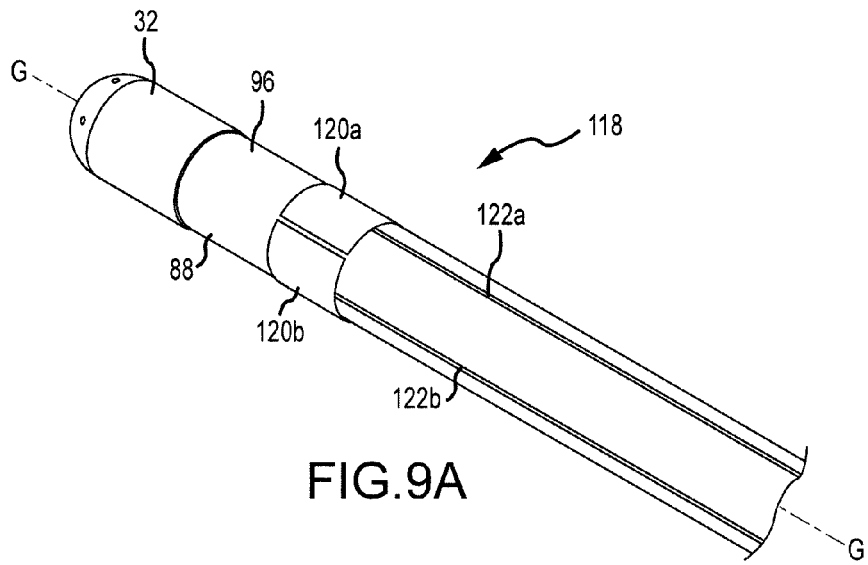
FIG. 9A is an isometric view of an embodiment of a portion of a catheter including electrodes and traces comprising printed ink in a first stage of construction.
Figure 9B:
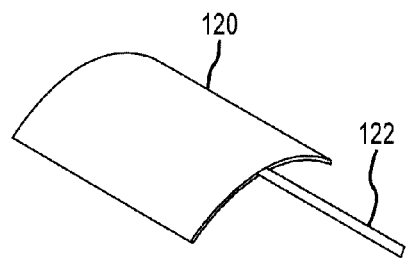
FIG. 9B is an isometric view of an electrode and a portion of a trace of the catheter portion of FIG. 9A.

FIG. 9A is an isometric view of an embodiment of a catheter 118 in a first stage of construction. FIG. 9B is an enlarged isometric view of an electrode 120 and portion of a trace 122 of the catheter 118. Referring to FIGS. 9A and 9B, the catheter 118 may include an elongate tubular body 88 defining an axis G, a tip electrode 32, a number of electrodes 120a, 120b, and a number of traces 122a, 122b. One or more of the electrodes 120 may not extend around the entire circumference of the body 88, but may instead extend around separate respective circumferential portions of the body 88. In an embodiment, each electrode 120 may extend around about a quarter or a third of the circumference of the body 88. In an embodiment, multiple electrodes 120 may be arranged in a circumferential set at substantially the same longitudinal position on the body 88. Although only a single circumferential set of electrodes 120 is illustrated in FIG. 9A, multiple such sets may be provided, in an embodiment. Such multiple sets (and the traces 122 electrically coupled with those sets) may be arranged (i.e., for traces of more distal electrodes 120 to extend longitudinally past more proximal electrodes 120) according to, for example only, one or more of the schemes shown in FIG. 3B (i.e., layered radially), in FIG. 7A (i.e., with traces routed through electrode gaps), or in FIGS. 8A-8D (i.e., with the majority of the length of the traces covered by an exterior layer).

FIG. 9A illustrates the catheter 118 after the tip electrode 32 has been coupled with the catheter body 88 and the electrodes 120 and traces 122 have been printed on a first layer 96 of the catheter body 88. The body first layer 96 may include one or more melt processing polymers, such as Pebax™, and/or another known appropriate material, such as Teflon™ or Kapton™. The body first layer 96 may be constructed, in an embodiment, similarly to the catheter body in FIG. 3A (i.e., with a distal segment of a first material and a proximal segment of a second material). The electrodes 120 and traces 122 may comprise electrically-conductive printed ink substantially as described herein.

Figure 9C:
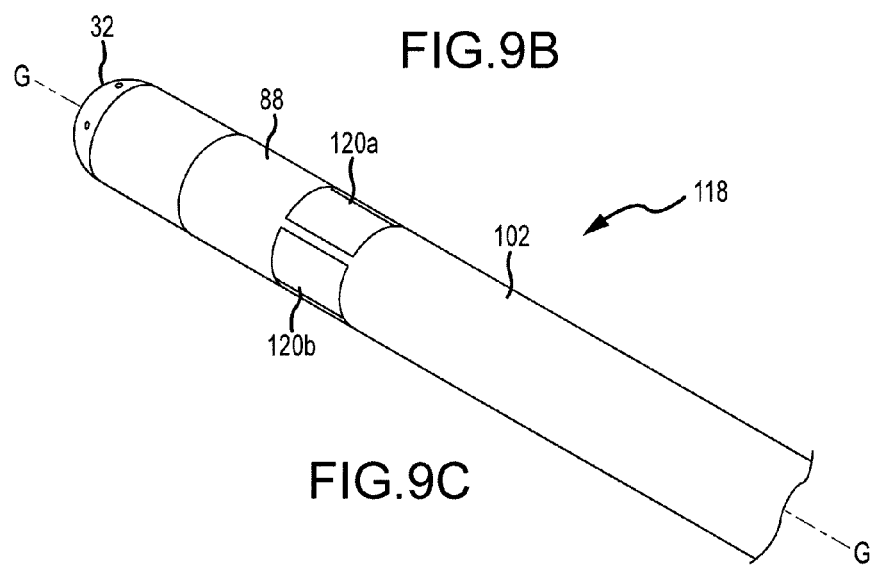
FIG. 9C is an isometric view of the catheter portion of FIG. 9A in a second stage of construction.

FIG. 9C is an isometric view of the catheter 118 in a second stage of construction. Referring to FIGS. 9A and 9C, after the electrodes 120 and traces 122 have been printed, a second body layer 102 may be printed. The second body layer 102 may cover (i.e., be radially-outward of) the traces 122. The second body layer 102 may also cover portions of the first body layer 96 not covered by the electrodes 120. In an embodiment, the second body layer 102 may comprise a dielectric ink.

The catheter and electrode arrangement illustrated in FIGS. 9A-9C may be preferred for directional position sensing—i.e., more localized positions of particular sides of the catheter. Such directional position sensing may be advantageous, for example, in a remote catheter guidance system (RCGS), such as one based on robotic movement of one or more medical devices. An exemplary embodiment of one such RCGS is shown in U.S. patent application publication no. 2009/0247993, which is hereby incorporated by reference in its entirety as though fully set forth herein.

Figure 10A:
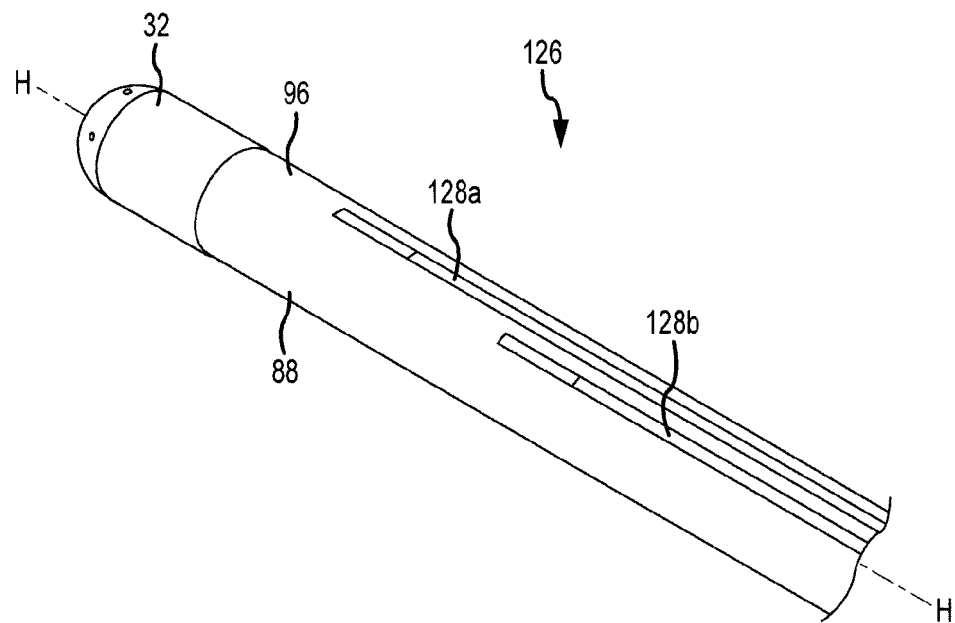
FIGS. 10A and 10B are isometric views of an embodiment of a portion of a catheter including electrodes and traces comprising printed ink in first and second stages of construction, respectively.

FIG. 10A is an isometric view of an embodiment of a catheter 126 in a first stage of construction. The catheter 126 may include an elongate tubular body 88 defining an axis H, a tip electrode 32, and a number of electrical traces 128a, 128b.

FIG. 10A illustrates the catheter 126 after the tip electrode 32 has been coupled with the catheter body 88 and the traces 128 have been printed on a first layer 96 of the catheter body 88. The body first layer 96 may include one or more melt processing polymers and/or another known appropriate material, such as Pebax™, Teflon™, or Kapton™. The body first layer 96 may be constructed, in an embodiment, similarly to the catheter body in FIG. 3A (i.e., with a distal segment of a first material and a proximal segment of a second material). The traces 128 may comprise electrically-conductive printed ink substantially as described herein.

Figure 10B:
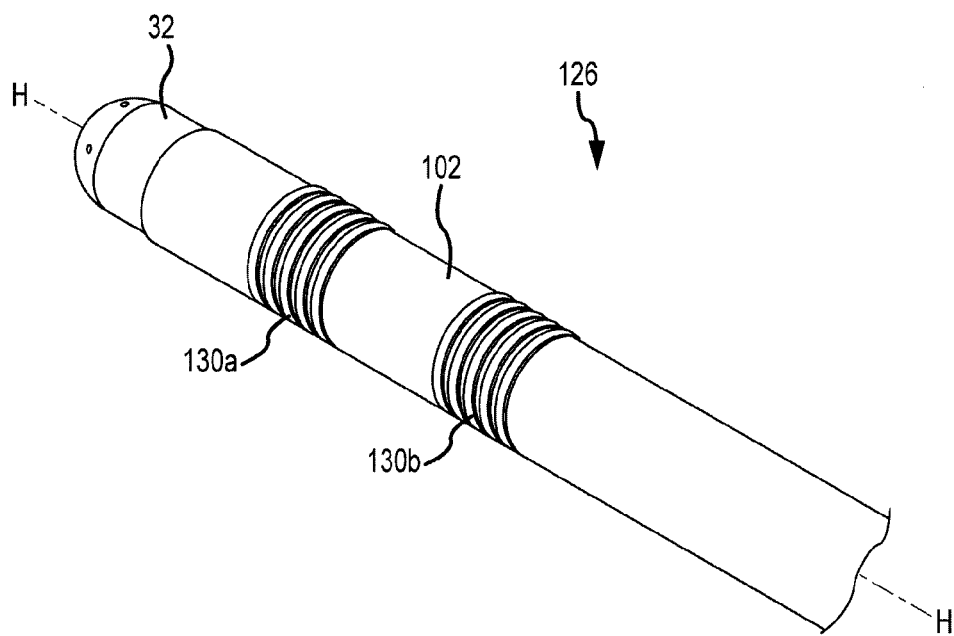

FIG. 10B is an isometric view of the catheter 126 in a second stage of construction. Referring to FIGS. 10A and 10B, after the traces 128a, 128b have been printed, electrodes 130a, 130b may be printed such that each electrode 130a, 130b is electrically coupled with a respective one of the traces 128a, 128b. Each electrode 130 may be printed as a series of rings, as a continuous spiral, or otherwise in a longitudinally-segmented arrangement. The electrodes 130 may comprise electrically-conductive ink, substantially as described herein. After the electrodes 130 are printed, a second body layer 102 may be printed. The second body layer 102 may cover (i.e., be radially-outward of) the traces 128, including the portions of the traces 128 longitudinally between segments of a given electrode 130. The second body layer 102 may also cover portions of the first body layer 96 not covered by the electrodes 130. In an embodiment, the second body layer 102 may comprise a dielectric ink.

The catheter 126 may be preferred for a relatively more flexible distal end. The electrodes 130, by virtue of the longitudinal gaps between segments, may flex and bend with the catheter body more than would a more longitudinally-continuous electrode, such as the electrodes 90 shown in FIGS. 7A-7F.

It should be understood that the features of the catheter embodiments 24, 42, 62, 86, 106, 118, 126 described and illustrated herein are not mutually-exclusive. Instead, features from different embodiments may be combined as desired for a given application. For example, the ring electrodes 90 of FIGS. 7A-7F may each extend about the entire circumference of the catheter body 88, in an embodiment, by radially layering their respective traces 92 according to the scheme illustrated in FIG. 3B. In another example, the electrodes 120 of FIGS. 9A-9C may be provided with the ribs 100 illustrated in FIGS. 7A-7F. Of course, numerous other combinations are possible and contemplated.

The aforementioned catheter embodiments 24, 42, 62, 86, 106, 118, 126 may operate with a variety of catheter systems such as visualization systems, mapping systems, and navigation support and positioning systems (i.e., for determining a position and orientation (P&O) of a flexible elongate member or other medical device). One such system is illustrated in FIG. 11.

Figure 11:
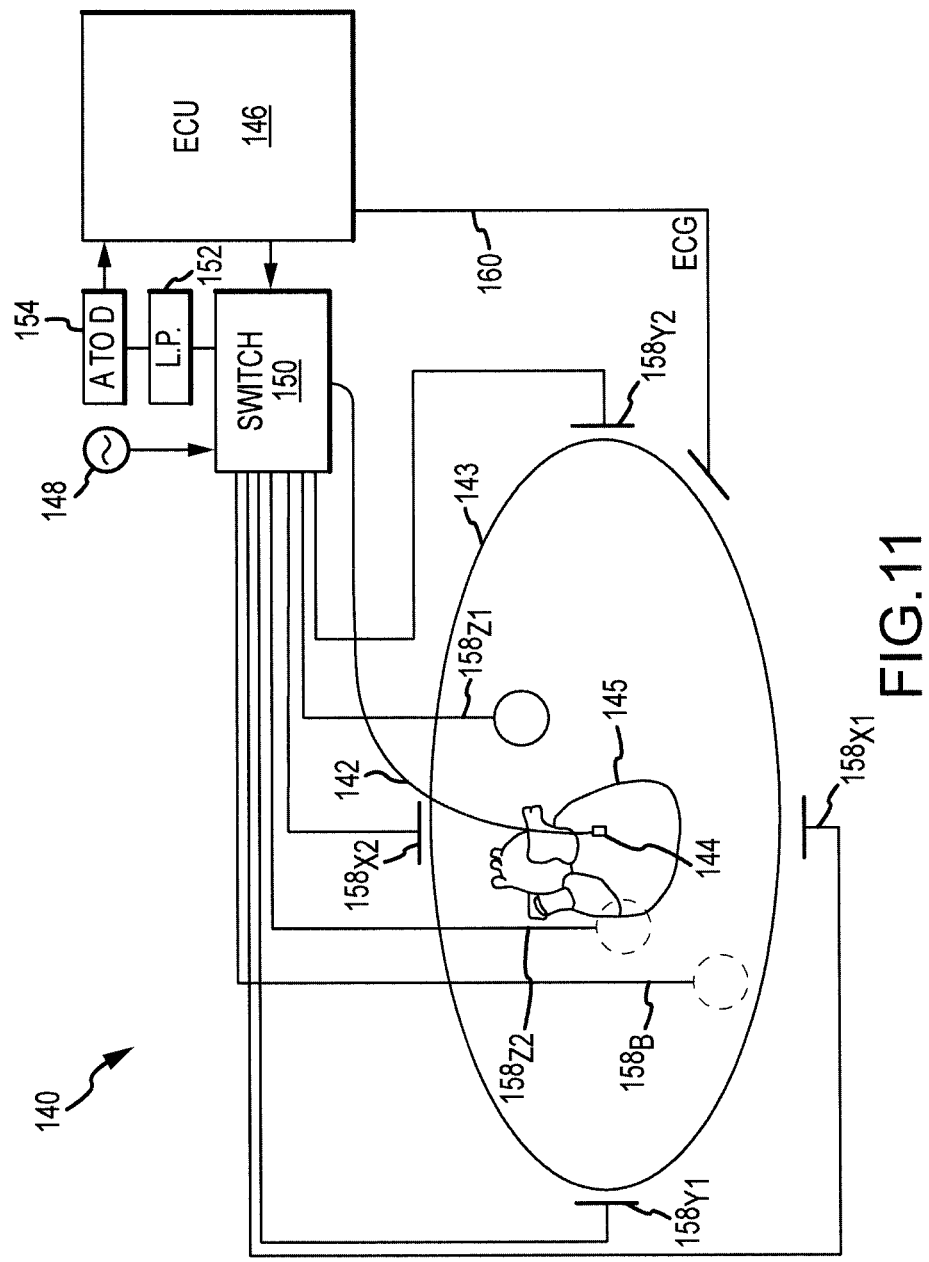
FIG. 11 is a schematic view of a medical device mapping and navigation system.
Figure 12A:
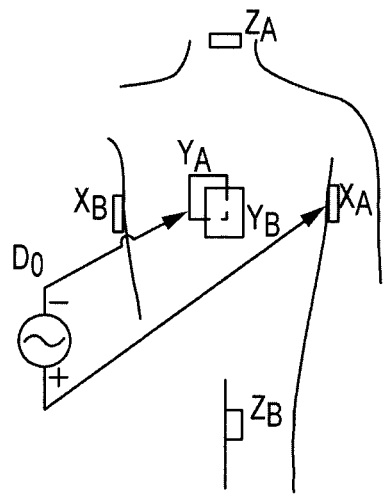
FIGS. 12A-12D are diagrammatic views of exemplary dipoles created using the mapping and navigation system of FIG. 11.
Figure 12B:
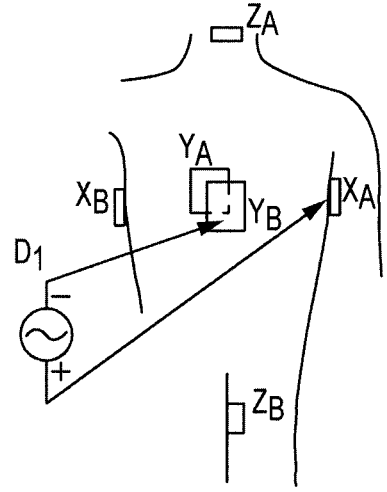
Figure 12C:
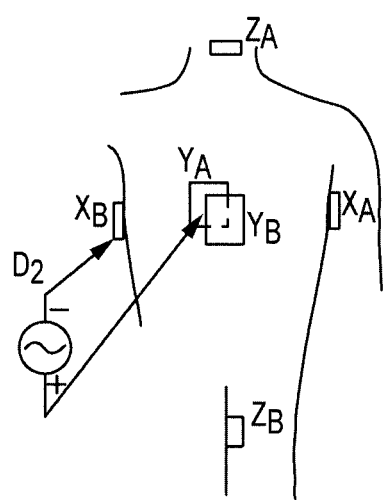
Figure 12D:
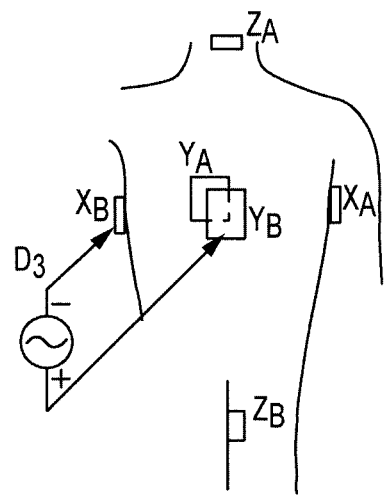

FIG. 11 is a schematic and diagrammatic view of an embodiment of a medical device mapping and navigation system 140. The system 140 is coupled with a catheter 142 that can be guided to and disposed in a portion of a body 143, such as a heart 145. The catheter 142 can include one or more sensors 144 for, e.g., collecting electrophysiology data, applying ablation energy, and/or determining a location of the catheter within the body. The system may include, at least in part, an electronic control unit (ECU) 146, a signal generator 148, a switch 150, a low-pass filter 152, an analog-to-digital (A-to-D) converter 154, a plurality of body surface electrode patches 156, and electrocardiogram (ECG) patches 160.

The system 140 is provided for visualization, mapping, and/or navigation of internal body structures and may be referred to herein as "the navigation system." The navigation system 140 may comprise an electric field-based system, such as, for example, an EnSite™ Velocity™ cardiac electro-anatomic mapping system running a version of EnSite™ NavX™ navigation and visualization technology software commercially available from St. Jude Medical, Inc., of St. Paul, Minn. and as also seen generally by reference to U.S. Pat. No. 7,263,397, or U.S. Patent Application Publication No. 2007/0060833 A1, both hereby incorporated by reference in their entireties as though fully set forth herein. In other exemplary embodiments, the navigation system 140 may comprise systems other than electric field-based systems. For example, the navigation system may comprise a magnetic field-based system such as the Carto™ system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein. In another exemplary embodiment, the navigation system 140 may comprise a magnetic field-based system based on the MediGuide™ technology available from St. Jude Medical, Inc., and as generally shown with reference to one or more of U.S. Pat. Nos. 6,233,476; 7,197,354; and 7,386,339, the disclosures of which are hereby incorporated by reference in their entireties as though fully set forth herein. In yet another embodiment, the navigation system 140 may comprise a combination electric field-based and magnetic field-based system, such as, for example and without limitation, the system described in pending U.S. patent application Ser. No. 13/231,284, or the Carto™ 3 system commercially available from Biosense Webster, and as generally shown with reference to U.S. Pat. No. 7,536,218, the disclosures of which are hereby incorporated by reference in their entireties as though set fully forth herein. In yet still other exemplary embodiments, the navigation system 140 may comprise or be used in conjunction with other commonly available systems, such as, for example and without limitation, fluoroscopic, computed tomography (CT), and magnetic resonance imaging (MRI)-based systems. For purposes of clarity and illustration only, the navigation system 140 will be described hereinafter as comprising an electric field-based system, such as, for example, the EnSite™ NavX™ system identified above.

The catheter 142 and sensors 144 may be provided for a variety of diagnostic and therapeutic purposes including, for example, electrophysiological studies, pacing, cardiac mapping, and ablation. In an embodiment, the catheter 142 can be an ablation catheter, mapping catheter, or other elongate medical device. The number, shape, orientation, and purpose of the sensors 144 may vary in accordance with the purpose of the catheter 142. In an embodiment, at least one sensor 144 can be an electrode. For purposes of illustration, the description below will be with respect to an embodiment in which the sensors 144 comprise one or more electrodes, but the disclosure is not limited to such an embodiment.

The catheter 142 may comprise any catheter embodiment 24, 42, 62, 86, 106, 118, 126 described herein, or another catheter including one or more features illustrated and/or described herein. Accordingly, the sensor 144 may comprise a printed-ink electrode (such as one or more of electrodes 32, 34, 90, 112, 120, 130 and/or another electrode including one or more features illustrated and/or described herein) and/or a printed-ink force sensor (such as force sensor 66).

With the exception of the patch electrode $158_B$ called a "belly patch," the patch electrodes 158 are provided to generate electrical signals used, for example, in determining the position and orientation of the catheter 142 and in the guidance thereof. In one embodiment, the patch electrodes 158 are placed generally orthogonally on the surface of the body and are used to create axes-specific electric fields within the body. For instance, in one exemplary embodiment, patch electrodes $158_{X1}$, $158_{X2}$ may be placed along a first (x) axis. Patch electrodes $158_{Y1}$, $158_{Y2}$ may be placed along a second (y) axis, and patch electrodes $158_{Z1}$, $158_{Z2}$ may be placed along a third (z) axis. Each of the patch electrodes 158 may be coupled to the multiplex switch 150. In an exemplary embodiment, the ECU 146 is configured, through appropriate software, to provide control signals to the multiplex switch 150 to thereby sequentially couple pairs of electrodes 158 to the signal generator 148. Excitation of each pair of electrodes 158 (e.g., in either orthogonal or non-orthogonal pairs) generates an electrical field within the patient's body 143 and within an area of interest such as the heart 145. Voltage levels at non-excited electrodes 158, which are referenced to the belly patch $158_B$, are filtered by low-pass filter 152 and converted by A-to-D converter 154 and provided to the ECU 146 for use as reference values.

As noted above, one or more electrodes 144 are mounted in or on the catheter 142. In an exemplary embodiment, at least one of the electrodes 144 comprises a positioning electrode and is configured to be electrically coupled to the ECU 146. With a positioning electrode 144 electrically coupled to the ECU 146, the electrode 144 is placed within electrical fields created in the body 143 (e.g., within the heart 145) by exciting the patch electrodes 158. The positioning electrode 144 experiences voltages that are dependent on the position of the positioning electrode 144 relative to the locations of the patch electrodes 158. Voltage measurement comparisons made between the electrode 144 and the patch electrodes 158 may be used to determine the position of the positioning electrode 144 relative to the heart 145 or other tissue. Movement of the positioning electrode 144 proximate a tissue (e.g., within a chamber of the heart 145) may produce information regarding the geometry of the tissue. This information may be used, for example, to generate models and maps of anatomical structures. Such maps and models may reflect a particular state of the anatomical structure such as, for example, the shape of the heart 145 at a particular point in the cardiac cycle. Position information determined according to measurements made with the electrode 144 may thus be associated with a particular portion of the cardiac cycle based on readings from the ECG patches 160. Information received from the positioning electrode 144 can also be used to display on a display device, the location and orientation of the positioning electrode 144 and/or a portion of the catheter 142 relative to the heart 145 or other tissue. Accordingly, among other things, the ECU 146 of the navigation system 140 may provide a means for generating display signals used to control a display and the creation of a graphical user interface (GUI) on the display.

The ECU 146 may comprise a programmable microprocessor or microcontroller, or may comprise an application specific integrated circuit (ASIC). The ECU 146 may include a an input/output (I/O) interface through which the ECU 146 may receive a plurality of input signals including, for example, signals generated by patch electrodes 158 and the positioning electrode 144 (among others), and generate a plurality of output signals including, for example, those used to control a display and other user interface components. The ECU 146 may be configured to perform various functions with appropriate programming instructions or code (i.e., software). Accordingly, the ECU 144 can be programmed with one or more computer programs encoded on a computer-readable storage medium for performing functionality described herein.

FIGS. 12A-12D show a plurality of exemplary non-orthogonal dipoles, designated $D_0$, $D_1$, $D_2$ and $D_3$. Referring to FIGS. 11 and 12A-12D, for any desired axis, the potentials measured across an intra-cardiac positioning electrode 144 resulting from a predetermined set of drive (source-sink) configurations may be combined algebraically to yield the same effective potential as would be obtained by simply driving a uniform current along the orthogonal axes. Any two of the surface electrodes 158 may be selected as a dipole source and drain with respect to a ground reference, e.g., belly patch $158_B$, while the unexcited body surface electrodes measure voltage with respect to the ground reference. The positioning electrode 144 placed in heart 145 is also exposed to the field from a current pulse and is measured with respect to ground, e.g., belly patch $158_B$. In practice, a catheter or multiple catheters within the heart may contain multiple positioning electrodes 144 and each positioning electrode 144 potential may be measured separately.

Data sets from each of the patch electrodes and the positioning electrode 144 are used to determine the location of the positioning electrode 144 within heart 145. After the voltage measurements are made, a different pair of surface electrodes is excited by the current source and the voltage measurement process of the remaining patch electrodes and positioning electrode 144 takes place. The sequence occurs rapidly, e.g., on the order of 100 times per second, in an embodiment. To a first approximation the voltage on the positioning electrode 144 within the heart bears a linear relationship with position between the patch electrodes that establish the field within the heart, as more fully described in U.S. Pat. No. 7,263,397 referred to above.

In summary, FIG. 11 shows an exemplary navigation system 140 that employs seven body surface electrodes (patches), which may be used for injecting current and sensing resultant voltages. Current may be driven between two patches at any time; some of those driven currents are illustrated in FIGS. 12A-12D. Measurements may be performed between a non-driven patch and, for example, belly patch $158_B$ as a ground reference. A patch bio-impedance, also referred to as a "patch impedance" may be computed according to the following equation:

$$BioZ[c \to d][e] = \frac{V_e}{I_{c \to d}} \quad (1)$$

where $V_e$ is the voltage measured on patch e and $I_{c \to d}$ is a known constant current driven between patches c and d, where patches c, d, and e may be any of the patch electrodes 158. The position of an electrode may be determined by driving current between different sets of patches and measuring one or more patch impedances along with the voltage on the positioning electrode. In one embodiment, time division multiplexing may be used to drive and measure all quantities of interest. Position determining procedures are described in more detail in U.S. Pat. No. 7,263,397 and publication no. 2007/0060833 referred to above, as well as other references.

Although a number of embodiments have been described above with a certain degree of particularity, those skilled in the art could make numerous alterations to the disclosed embodiments without departing from the spirit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of this disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An elongate medical device comprising:
    an elongate tubular body defining a longitudinal axis;
    a first electrode that extends circumferentially about a portion of said elongate tubular body, said first electrode defining a circumferential gap;
    a second electrode that extends around the entire circumference of said elongate tubular body;
    a first trace comprising electrically-conductive ink, electrically coupled with said first electrode, extending longitudinally from said first electrode along a surface of said elongate tubular body; and
    a second trace comprising electrically-conductive ink, electrically coupled with said second electrode and electrically isolated from said first electrode, extending longitudinally through said circumferential gap of said first electrode;
    wherein at least one of said first electrode and said second electrode comprises a plurality of ribs.

2. The elongate medical device of claim 1, wherein said first electrode comprises electrically-conductive ink.

3. The elongate medical device of claim 1, wherein said ribs extend longitudinally.

4. The elongate medical device of claim 1, further comprising an outer layer radially-outward of at least a portion of said first trace, said second trace, or said first trace and said second trace, wherein said outer layer comprises a dielectric material.

5. The elongate medical device of claim 4, wherein said outer layer comprises dielectric printed ink.

6. The elongate medical device of claim 1, wherein at least one of said first electrode and said second electrode comprises a first conductive ink having a lower impedance than a second conductive ink comprising at least one of said first trace and said second trace.

7. The elongate medical device of claim 1, wherein said body comprises a distal segment and a proximal segment, at least one of said first electrode and said second electrode is disposed on said distal segment, said distal segment comprises a first polymer, said proximal segment comprises a second polymer, and said second polymer has a lower melting point than said first polymer.

8. The elongate medical device of claim 1, wherein said second electrode is longitudinally distal of said first electrode.

9. The elongate medical device of claim 1, further comprising:
a third electrode that extends circumferentially about a portion of said elongate tubular body, said third electrode defining a third electrode circumferential gap, said third electrode disposed longitudinally proximal of said first electrode;
wherein said first trace and said second trace extend longitudinally through said third electrode circumferential gap.

10. The elongate medical device of claim 9, further comprising a third trace comprising electrically-conductive ink, electrically coupled with said third electrode, extending longitudinally from said third electrode.

11. The elongate medical device of claim 10, wherein said first, second, and third traces are parallel with each other.

12. The elongate medical device of claim 1 wherein said first trace and said second trace are printed directly on said elongate tubular body.

13. The elongate medical device of claim 1, wherein said ribs extend circumferentially.

14. The elongate medical device of claim 1, further comprising a handle coupled to a proximal end portion of said elongate tubular body, the handle comprising an electromechanical connector, wherein said first trace and said second trace are electrically accessible through said electromechanical connector.

15. An elongate medical device comprising:
an elongate tubular body defining a longitudinal axis;
a first electrode that extends circumferentially about a portion of said elongate tubular body;
a second electrode that extends circumferentially about a portion of said elongate tubular body, said second electrode defining a circumferential gap;
a trace comprising electrically-conductive ink, electrically coupled with said first electrode, extending longitudinally from said first electrode along a surface of said elongate tubular body through said circumferential gap; and
an outer layer radially-outward of at least a portion of said trace, wherein said outer layer comprises a printed ink dielectric material, further wherein said printed ink dielectric material does not cover any portion of said first electrode.

16. The elongate medical device of claim 15, wherein said first electrode and said second electrode comprise electrically-conductive ink.

17. The elongate medical device of claim 16, wherein said first electrode, said second electrode, and said trace are printed directly on said elongate tubular body.

18. The elongate medical device of claim 17, wherein said elongate tubular body comprises polymer.

19. The elongate medical device of claim 15, wherein said trace is a first trace, further comprising:
a second trace comprising electrically-conductive ink, electrically coupled with said second electrode and extending longitudinally from said second electrode along said surface of said elongate tubular body;
wherein said printed ink dielectric material of said outer layer is radially-outward of at least a portion of said second trace.

\* \* \* \* \*